US011672700B2

(12) United States Patent
Olson

(10) Patent No.: US 11,672,700 B2
(45) Date of Patent: Jun. 13, 2023

(54) ADJUSTABLE LOOP FIBER OPTIC ILLUMINATION DEVICE FOR SURGERY

(71) Applicant: The Regents of the University of Colorado, Denver, CO (US)

(72) Inventor: Jeffrey L. Olson, Cherry Hills Village, CO (US)

(73) Assignee: The Regents of the University of Colorado, Denver, CO (US)

( * ) Notice: Subject to any disclaimer, the term of this patent is extended or adjusted under 35 U.S.C. 154(b) by 67 days.

(21) Appl. No.: 17/125,109

(22) Filed: Dec. 17, 2020

(65) Prior Publication Data

US 2021/0346194 A1 Nov. 11, 2021

Related U.S. Application Data

(63) Continuation of application No. 16/209,470, filed on Dec. 4, 2018, now Pat. No. 10,898,371, which is a continuation of application No. 14/438,532, filed as application No. PCT/US2013/066837 on Oct. 25, 2013, now Pat. No. 10,179,067.

(60) Provisional application No. 61/718,543, filed on Oct. 25, 2012.

(51) Int. Cl.
*A61F 9/007* (2006.01)
*A61B 3/00* (2006.01)
*A61B 90/30* (2016.01)

(52) U.S. Cl.
CPC ............ *A61F 9/007* (2013.01); *A61B 3/0008* (2013.01); *A61B 90/30* (2016.02); *A61B 2090/306* (2016.02)

(58) Field of Classification Search
CPC .... A61F 9/0007; A61F 3/0008; A61F 3/0075; A61F 90/30; A61F 2090/306
See application file for complete search history.

(56) References Cited

U.S. PATENT DOCUMENTS

| 4,326,530 | A | * | 4/1982 | Fleury, Jr. | ............... | A61B 18/14 |
| | | | | | | 606/47 |
| 5,123,906 | A | | 6/1992 | Kelman | | |
| 5,163,942 | A | * | 11/1992 | Rydell | ............. | A61B 17/32056 |
| | | | | | | 606/1 |
| 5,171,314 | A | * | 12/1992 | Dulebohn | ........ | A61B 17/32056 |
| | | | | | | 606/113 |
| 5,417,684 | A | * | 5/1995 | Jackson | ........... | A61B 17/32056 |
| | | | | | | 606/1 |
| 5,822,036 | A | * | 10/1998 | Massie | ................... | A61B 3/125 |
| | | | | | | 351/219 |

(Continued)

FOREIGN PATENT DOCUMENTS

| JP | H0451946 | 2/1992 |
| JP | 2007535341 | 12/2007 |

(Continued)

OTHER PUBLICATIONS

Extended European Search Report and Search Opinion dated May 10, 2016 for European Application No. 13849319.2.

*Primary Examiner* — Eric S Gibson
(74) *Attorney, Agent, or Firm* — DLA Piper LLP (US)

(57) ABSTRACT

The present disclosure provides an adjustable endoscopic surgical device for illuminating a tissue surface with diffuse and oblique light. In some embodiments, light emanates from the sides of an optical fiber, which is optionally formed at least in part into a loop shape.

18 Claims, 5 Drawing Sheets

(56) References Cited

U.S. PATENT DOCUMENTS

| | | | | |
|---|---|---|---|---|
| 6,221,028 B1* | 4/2001 | Lieberman | | A61B 3/14 351/200 |
| 6,367,984 B1* | 4/2002 | Stephenson | | G02B 6/3825 385/76 |
| 6,676,668 B2* | 1/2004 | Mercereau | | A61B 17/221 606/1 |
| 7,197,931 B2* | 4/2007 | Kim | | G01N 29/07 356/482 |
| 7,428,350 B1* | 9/2008 | Varadarajan | | G01K 11/32 374/E11.015 |
| 7,985,028 B2* | 7/2011 | Aoki | | G02B 6/2551 385/39 |
| 8,771,297 B2* | 7/2014 | Miller | | A61B 17/12013 606/139 |
| 8,974,473 B2* | 3/2015 | Kaplan | | A61B 17/12013 606/205 |
| 9,265,526 B1* | 2/2016 | Abdou | | A61B 17/3439 |
| 9,433,475 B2* | 9/2016 | Bierbaum | | A61B 18/22 |
| 9,498,206 B2* | 11/2016 | Fung | | A61B 17/0469 |
| 9,936,956 B2* | 4/2018 | Fung | | A61B 17/12013 |
| 10,179,067 B2* | 1/2019 | Olson | | A61B 90/30 |
| 10,898,371 B2* | 1/2021 | Olson | | A61F 9/007 |
| 2006/0184162 A1* | 8/2006 | Smith | | A61B 3/0008 606/4 |
| 2007/0100326 A1* | 5/2007 | Smith | | A61F 9/007 606/4 |
| 2007/0293748 A1* | 12/2007 | Engvall | | A61B 5/0059 600/371 |
| 2010/0228119 A1* | 9/2010 | Brennan | | A61B 5/0066 600/424 |
| 2011/0044577 A1* | 2/2011 | Gupta | | G01B 11/16 385/13 |
| 2011/0144641 A1* | 6/2011 | Dimalanta, Jr. | | A61B 18/1477 606/45 |
| 2011/0144745 A1* | 6/2011 | Martin | | A61B 90/30 623/4.1 |
| 2012/0022424 A1* | 1/2012 | Yamamoto | | A61F 9/00781 604/8 |
| 2012/0165941 A1* | 6/2012 | Rabiner | | A61B 17/8833 623/17.12 |
| 2014/0288417 A1* | 9/2014 | Schmidtlin | | A61B 3/102 600/425 |
| 2015/0025325 A1* | 1/2015 | Lee | | A61B 90/30 600/249 |
| 2015/0282888 A1* | 10/2015 | Olson | | A61B 90/30 600/249 |
| 2015/0351958 A1* | 12/2015 | Contiliano | | A61M 25/0662 604/164.11 |
| 2017/0014023 A1* | 1/2017 | Kern | | A61B 1/07 |
| 2019/0175398 A1* | 6/2019 | Olson | | A61B 90/30 |
| 2021/0346194 A1* | 11/2021 | Olson | | A61B 90/30 |

FOREIGN PATENT DOCUMENTS

| | | |
|---|---|---|
| WO | WO2008/124492 A1 | 10/2008 |
| WO | WO2011/081525 A1 | 7/2011 |
| WO | WO2011/150045 A1 | 12/2011 |

* cited by examiner

ADJUSTABLE LOOP FIBER OPTIC ILLUMINATION DEVICE FOR SURGERY

PRIORITY CLAIM

This application is a continuation of U.S. patent application Ser. No. 16/209,470 filed Dec. 4, 2018, which is a continuation of U.S. patent application Ser. No. 14/438,532 filed Apr. 24, 2015, which is a U.S. 371 national stage of International Patent Application No. PCT/US2013/066837 filed Oct. 25, 2013, which claims priority to U.S. Patent Application Ser. No. 61/718,543 filed Oct. 25, 2012, the entire contents of each of which are incorporated herein by reference and relied upon.

BACKGROUND

During intraocular or endoscopic surgery, a surgeon may need to alter both the intensity and the direction of light in order to better visualize the surgical field. Conventional light sources often work similar to a flashlight, with a directed beam that focuses light directly on a specific area. This direct illumination prevents the surgeon from fully visualizing any texture or surface irregularities. Consequently, surgeons often employ special stains or dyes to help visualize the surgical field. For example, during vitreoretinal surgery for an epiretinal membrane, direct illumination of the membrane is often inadequate to visualize the tissue, so vital stains may be used to increase visibility of the tissue.

Handheld lights that provide direct illumination typically have a field of illumination of about 50 to 80 degrees. This direct illumination fails to highlight the texture of a surface. Further, reducing the distance between the light and the surface of the retina increases the risk of phototoxicity to retinal photoreceptors. Wide-field chandelier lighting systems typically have a 100 degree field of illumination, but are placed at a fixed distance from the retina and therefore cannot provide side illumination to highlight surface texture. Further, chandeliers cast shadows when working instruments are placed in front of them and are also prone to creating glare during air-fluid exchanges such as those required during vitrectomy. Further, chandeliers are often incapable of homogenously illuminating the entire eye, and often need to be repositioned during surgery. Further, the tips of chandelier lights or probes are prone to melting if they come into contact with blood or uveal tissue. Existing fiber optic illumination systems provide direct or wide-field illumination only. A need exists for improved surgical lighting system, especially those effective for visualizing the surface details of ocular tissue.

SUMMARY

This adjustable fiber optic illumination device invention allows the surgeon to adjust both the direction and the intensity of light intraoperatively, so that the surgical field can be illuminated from the side or in a more diffuse manner, thereby increasing contrast and visualization of surface texture and irregularities, thereby eliminating or reducing the need for intraoperative stains or dyes.

Accordingly, the present disclosure provides a surgical illumination device comprising an optical fiber extending through the lumen and comprising a distal end and a proximal end; a stem comprising a lumen, wherein the optical fiber and the proximal end are housed within the lumen to form a loop portion defining a loop length; an adjuster operably coupled to the proximal end, wherein movement of the adjuster causes the loop length to change; and a light source operably coupled to the distal end.

In some embodiments, the present disclosure provides a method of illuminating ocular tissue, the method comprising providing a device as described herein; optionally increasing the loop length such that the loop portion has a diameter larger than an eye or a portion thereof; placing the loop portion in proximity to the eye; and reducing the loop length such that the loop portion is stationary with respect to the eye.

DETAILED DESCRIPTION

Figure 1:
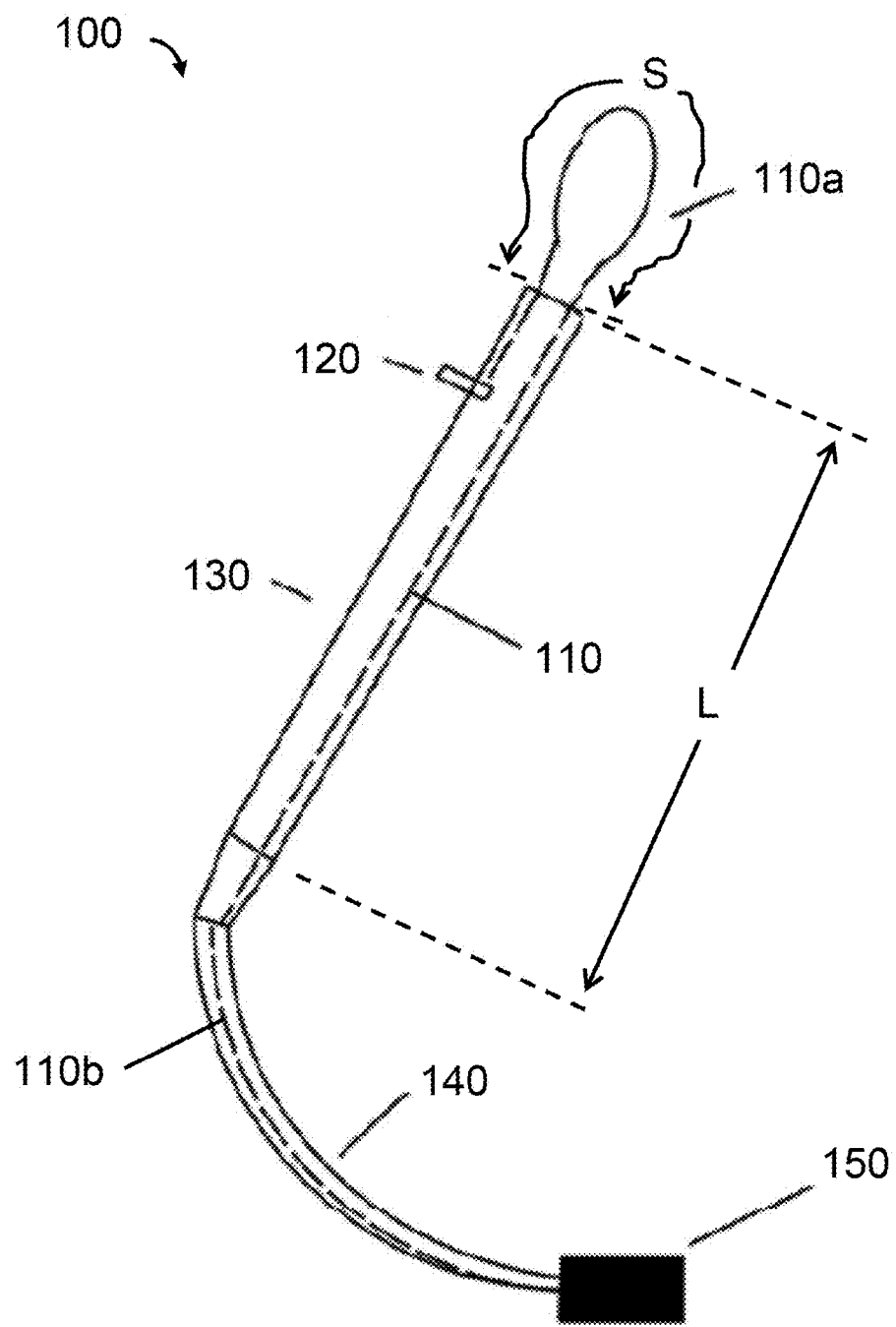
FIG. 1 illustrates one embodiment of a device according to the present disclosure.

In some embodiments, the present disclosure provides a device comprising a stem operably linked to a light source by a fiber optic cable. An optical fiber (also referred to as a fiber optic or a fiber optic element) passes through a lumen of the stem and a tip of the fiber optic is passed back into the lumen of the stem such that a loop is formed in the fiber optic. The tip of the fiber optic is operably coupled to an adjuster (e.g., a lever) which, when adjusted, causes the length of the fiber optic forming the loop portion to increase or decrease as needed. A second tip of the fiber optic is operably coupled to a light source, such as that associated with an endoscope. In some embodiments, the fiber optic and the endoscope are operably coupled by an adapter.

In some embodiments, the stem has a length of about 4 to 6 inches in length, for example about 4 inches, about 4.1 inches, about 4.2 inches, about 4.3 inches, about 4.4 inches, about 4.5 inches, about 4.6 inches, about 4.7 inches, about 4.8 inches, about 4.9 inches, about 5 inches, about 5.1 inches, about 5.2 inches, about 5.3 inches, about 5.4 inches, about 5.5 inches, about 5.6 inches, about 5.7 inches, about 5.8 inches, about 5.9 inches, or about 6 inches.

In some embodiments, the stem is a hollow tube shape having a regular or irregular cross-section, such as a circle, an oval, an ellipse, a square, a rounded square, etc. Generally, the stem has a cross-sectional area sufficient to permit the fiber optic to pass through (or partially pass through) at least two times. For vitrectomy surgery, the diameter of the stem may range from about 18 gauge to about 30 gauge, for example about 18 gauge, about 19 gauge, about 20 gauge, about 21 gauge, about 22 gauge, about 23 gauge, about 24 gauge, about 25 gauge, about 26 gauge, about 27 gauge, about 28 gauge, about 29 gauge, or about 30 gauge.

In some embodiments, the optical fiber is a flexible rod. In some embodiments, the optical fiber comprises, consists of, or consists essentially of glass, silica, or plastic. In some embodiments, the optical fiber has a diameter of about 50 μm to about 1000 μm, for example about 50 μm, about 60

μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, about 200 μm, about 210 μm, about 220 μm, about 230 μm, about 240 μm, about 250 μm, about 260 μm, about 270 μm, about 280 μm, about 290 μm, about 300 μm, about 310 μm, about 320 μm, about 330 μm, about 340 μm, about 350 μm, about 360 μm, about 370 μm, about 380 μm, about 390 μm, about 400 μm, about 410 μm, about 420 μm, about 430 μm, about 440 μm, about 450 μm, about 460 μm, about 470 μm, about 480 μm, about 490 μm, about 500 μm, about 510 μm, about 520 μm, about 530 μm, about 540 μm, about 550 μm, about 560 μm, about 570 μm, about 580 μm, about 590 μm, about 600 μm, about 610 μm, about 620 μm, about 630 μm, about 640 μm, about 650 μm, about 660 μm, about 670 μm, about 680 μm, about 690 μm, about 700 μm, about 710 μm, about 720 μm, about 730 μm, about 740 μm, about 750 μm, about 760 μm, about 770 μm, about 780 μm, about 790 μm, about 800 μm, about 810 μm, about 820 μm, about 830 μm, about 840 μm, about 850 μm, about 860 μm, about 870 μm, about 880 μm, about 890 μm, about 900 μm, about 910 μm, about 920 μm, about 930 μm, about 940 μm, about 950 μm, about 960 μm, about 970 μm, about 980 μm, about 990 μm, or about 1000 μm.

In some embodiments, light emanates from the sides or wall of the device depending upon its construction. In some embodiments, the optical fiber is housed in a cable, which contains the optical fiber and connects the stem of the device to a suitable light source via an adapter. The optical fiber extends through the lumen of the stem. The end of the optical fiber is attached to a lever, and a loop of the optical fiber passes out the distal end of the stem. It is this exposed portion of the optical fiber which illuminates the surgical field. The loop is retractable and expandable, thereby changing the amount of illumination, by sliding the lever and causing the size of the loop outside the stem to increase or decrease in diameter.

The optical fiber is necessary to transmit light from a suitable light source to the surgical field. The stem and cable are both necessary to house the optical fiber. The lever is necessary to change the size of the fiber optic loop outside the stem. In one embodiment, the lever could be removed, leaving a fixed amount of loop exposed.

In some embodiments, the tip of the optical fiber is operably coupled to a button or a sliding shaft instead of a lever. Alternatively, a sliding cover could be placed over the stem itself, whereby adjustment of the loop portion is achieved by advancing or retracting the sliding cover relative to the stem.

In some embodiments, the stem further comprises a flange suitable for anchoring the device in place when attached to or passed through the sclera.

In another embodiment, two or more optical fiber elements emanate from the of the stem, thus forming two or more fiber optic loop portions.

Thus, in one embodiment, the present disclosure provides surgical device comprising an optical fiber, wherein the optical fiber comprises a loop. In some embodiments, at least a portion of the optical fiber is housed in a stem. In some embodiments, a proximal end of the optical fiber is operably coupled to an adjuster. In some embodiments, the adjuster is configured to adjust a size associated with the loop. In some embodiments, the adjuster comprises a lever, a button, a sliding shaft or a sliding cover.

In another embodiment, the present disclosure comprises a surgical illumination device comprising an optical fiber extending through the lumen and comprising a distal end and a proximal end; a stem comprising a lumen, wherein the optical fiber and the proximal end are housed within the lumen to form a loop portion defining a loop length; and an adjuster operably coupled to the proximal end, wherein movement of the adjuster causes the loop length to change, wherein the distal end of the optical fiber is configured for coupling to a light source. In some embodiments, the surgical illumination device comprises an optical fiber cable surrounding at least a portion of the optical fiber. In some embodiments, the adjuster is a lever, a button, a sliding shaft or a sliding cover. In some embodiments, the stem comprises a flange configured to and suitable for anchoring the device in or through ocular tissue.

In some embodiments, a device as disclosed herein comprises or is configured in a first mode wherein light emanates from the loop and comprises or is configured in a second configuration wherein light emanates from a tip of the optical fiber. In some embodiments, the device is configured to convert from the first configuration to the second configuration during surgery.

FIG. 1 illustrates a device 100 according to the present disclosure including an optical fiber 110 comprising a fiber optic loop portion 110a. The optical fiber 110 has a proximal end 112 that is operably connected to an adjuster 120. The adjuster 120 is housed in a stem 130 which is configured to allow the adjuster 120 to slide along the length L of stem 130. Movement of the adjuster 120 along length L of the stem 130 causes the size S of the fiber optic loop 110a to change. A distal end of stem 130 is operably connected to a fiber optic cable 140 that houses a distal end portion 110b of the optical fiber 110. An adapter 150 is connected to the fiber optic cable 140 and enables the device 110 to be connected to a light source (not shown).

Figure 2:
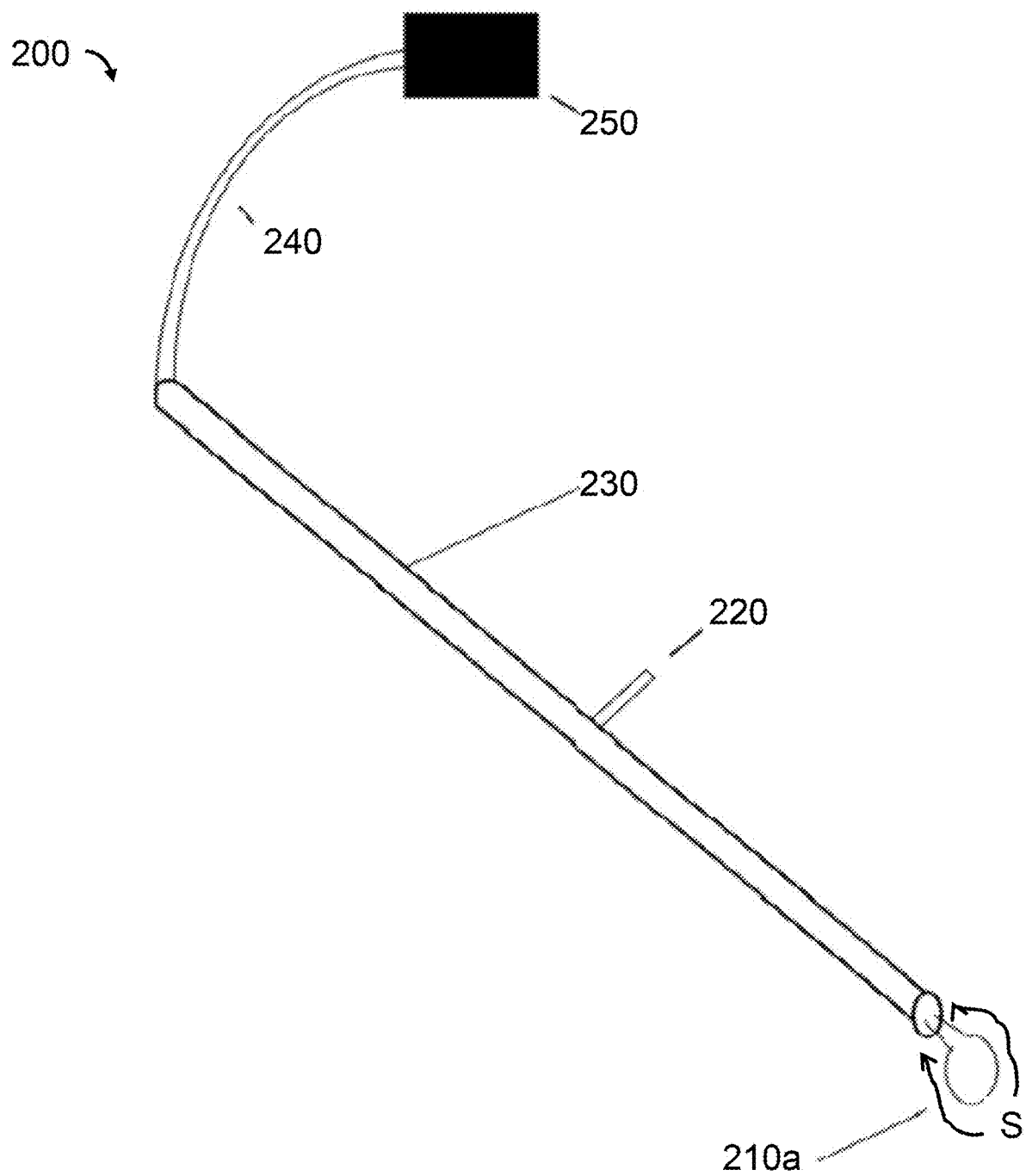
FIG. 2 illustrates another embodiment of a device according to the present disclosure.

FIG. 2 shows an external view of another embodiment of the present disclosure. In this embodiment, device 200 includes a fiber optic loop portion 210a extends from a stem 230 that is configured with an adjuster 220 that is a lever. Movement of the adjuster 220 changes the size S of the fiber optic loop portion 210a. Stem 230 is operably connected to a fiber optic cable 240 which in turn is connected to an adapter 250 that enables device 200 to be connected to a light source.

Figure 3C:
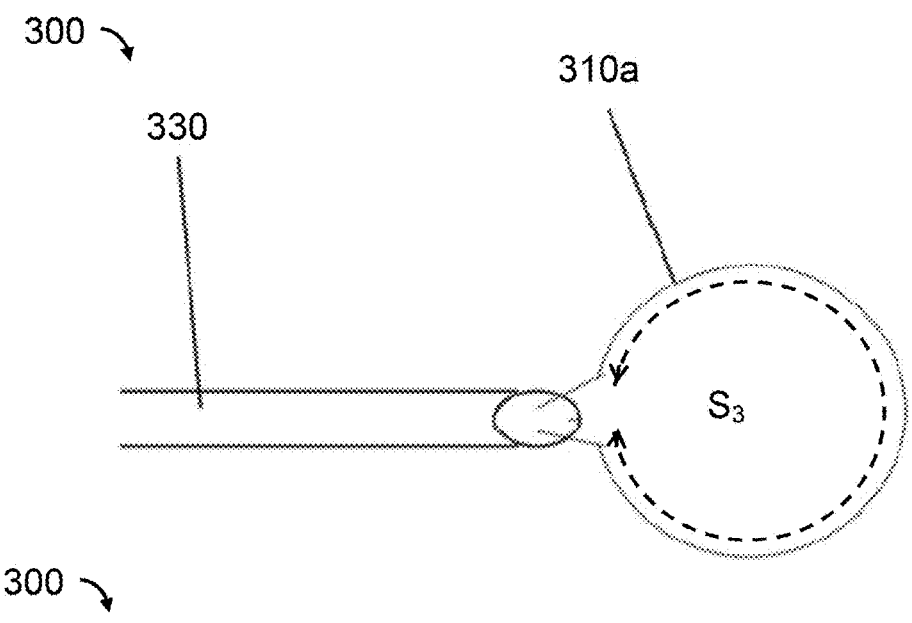
FIGS. 3A-3C depict an embodiment of a device according to the present invention wherein the size of the fiber optic loop is adjustable from a small size (FIG. 3A) to an intermediate size (FIG. 3B) to a large size (FIG. 3C), or vice versa.
Figure 3B:
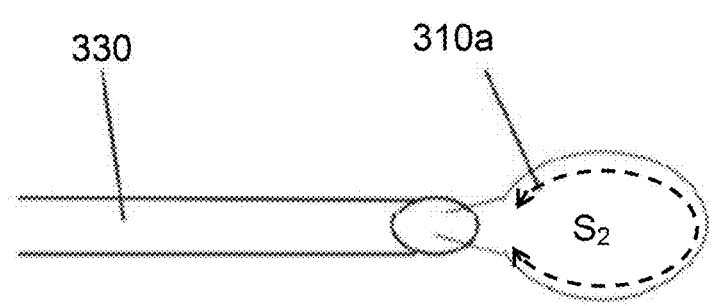
Figure 3A:
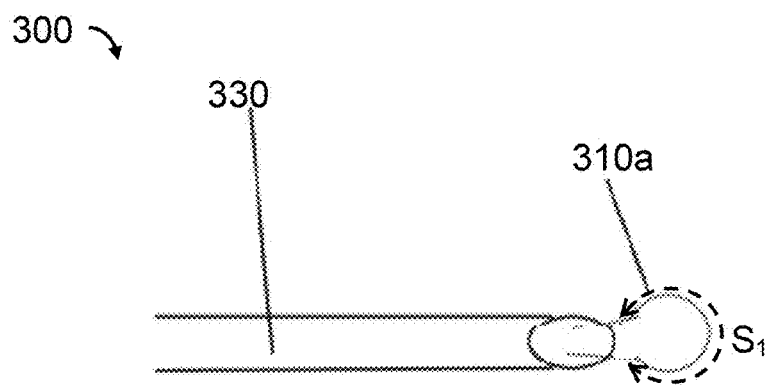

FIGS. 3a-3c illustrate the adjustment of fiber optic loop portion 310a in a device 300 consistent with the present disclosure. In this embodiment, device 300 includes a stem 330 that houses an optical fiber (not shown) which includes a fiber optic loop portion 310a. The fiber optic loop portion 310a extends from a proximal end of the stem 330. Movement of an adjuster (not shown) changes the size (S1-S3) of the fiber optic loop portion 310a. For example, fiber optic loop portion 310a may have an initial size S1 as shown in FIG. 3a. In some embodiments, such a configuration is useful for initial penetration or deployment of the device 300 during a surgical procedure. Movement of the adjuster (e.g., after initial deployment of the device 300 during a surgical procedure) may then cause the size of the fiber optic loop 310a to expand to a second size S2 as shown in FIG. 3b. If desired, additional movement of the adjuster causes the fiber optic loop portion 310a to further expand to a third size S3 as shown in FIG. 3c. Movement of the adjuster in an opposite direction may cause the fiber optic loop portion 310a to shrink, for example from an expanded size S3 (FIG. 3c) to an intermediate size S2 (FIG. 3b) and/or to a small size S1 (FIG. 3a).

In some embodiments, the fiber optic loop could be made much larger so that it could encompass the external diameter of the eye. This loop could then be placed around the equator of the eye during vitreoretinal surgery and tightened to a sufficient length to indent the eye wall, which aids the surgeon in visualizing the periphery of the retina as is done in scleral depression. Further, the added light from this would assist in visualizing any peripheral retinal pathology.

In some embodiments, the fiber optic loop can be used as a tool for pushing, pulling, or grasping an object (e.g., a tissue or a foreign body) during a surgical procedure. In some embodiments, the device is used to repair retinal detachments during a vitrectomy. In one such embodiment, the device is passed through a small gauge trocar or surgical wound. Once inside the eye, the adjuster is used to deploy (e.g., expand) the fiber optic loop. The fiber optic loop is then used to manually push the retina back against the eye wall. During this, the subretinal fluid can be drained through the lumen of the stem. Once the retina is reattached, a laser endoprobe is used to apply photocoagulation around the retinal tear.

In another instance, a vitrectomy may be performed to remove a dislocated intraocular lens or an intraocular foreign body. In one embodiment, a device according to the present disclosure is passed through a small gauge trocar or surgical wound. Once inside the eye, the adjuster is used to deploy (e.g., expand) the fiber optic loop. The fiber optic loop is then used to ensnare the intraocular lens or foreign body and remove it from the eye.

In another embodiment, retained lens material following cataract surgery can be chopped using a device according to the present disclosure as a snare. The lens material is first grasped in the fiber optic loop. The adjuster is then used to retract the fiber optic loop back into the stem, causing the lens material to split. The adjuster is then used to re-deploy the fiber optic loop, and the process can be repeated as many times as necessary to reduce the lens material to such a size that it can be removed with a vitreous cutter or simple aspiration.

Figure 4:
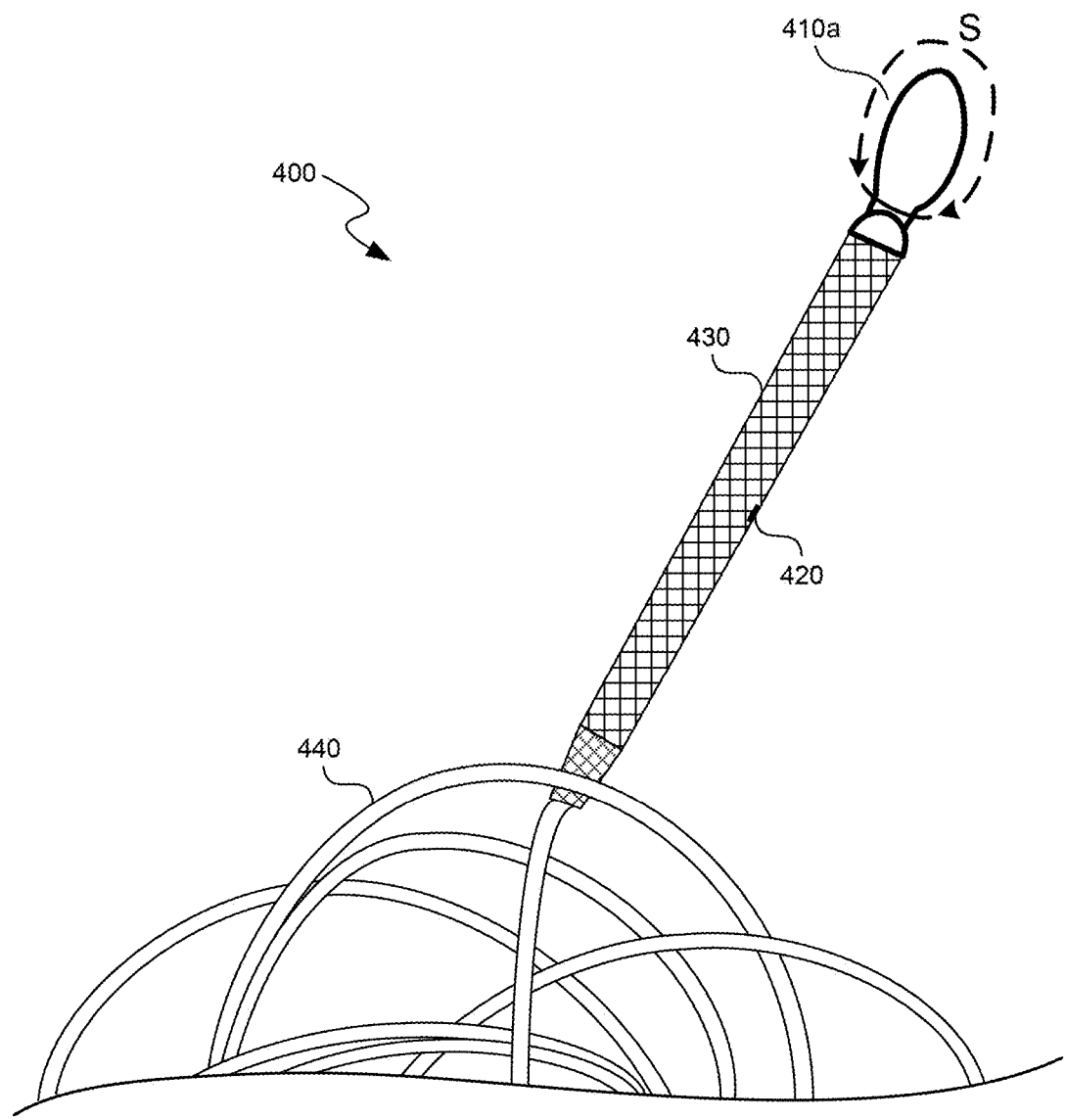
FIG. 4 illustrates another embodiment of a device according to the present disclosure wherein light emanates from the sides of the fiber optic loop.

By adjusting the length or size of the fiber optic loop, a surgeon may change the configuration of the end of the optical fiber itself intraoperatively. In contrast to prior art illumination devices, the device of the present disclosure offers a wider range of illumination options. For example, light emanates from the sides of the devices disclosed herein, rather than from the tip. For example, as shown in FIG. 4, a device 400 consistent with the present disclosure includes an illuminated fiber optic loop portion 410a which extends adjustably from a stem 430. Stem 430 is connected to a fiber optic cable 440 that is in turn operably connected to an adapter (not shown). The adapter is connected to a light source (not shown) which provides light to the optical fiber and the fiber optic loop portion 410a. Movement of adjuster 420 (e.g., a lever) causes size S of the illuminated fiber optic loop portion 410a to expand or shrink. In addition, the fiber optic loop portion of devices of the present disclosure can be used to push or hold tissue during surgery.

With conventional lighting systems, such as a vitrectomy light pipe, the light is directed perpendicular to the surgical field, similar to the way a flashlight is used. This provides bright, focused light for working, but can be too intense when the surgeon needs to hold the light closer to the tissue. Specifically, within the eye, this can lead to too much light, or phototoxicity to retinal photoreceptors and subsequent visual loss. Further, this direct illumination does not highlight the texture of the tissue's surface, which is often desirable during such surgical procedures as epiretinal membrane peeling. To overcome this shortcoming, surgeons may employ the use of vital dyes such as indocyanine green to visualize this tissue better. These dyes can add to the time, cost, and risk of the surgery.

With the present invention, the light supplied during surgery is more diffuse, thus decreasing the risk of phototoxicity to retinal photoreceptors. This is accomplished by using the light that emanates from the sides of the optical fiber, which in an exemplary embodiment may be a loop at the tip of the instrument. This loop can be made larger or smaller during surgery as dictated by the surgeon's needs. Making the loop larger provides more light, and making the loop smaller decreases the light. Further, the loop can be used to light the surface of the retina from an oblique angle, which facilitates visualizing the texture of the retinal surface, thereby decreasing the need for intraoperative vital dyes. Further, the loop of the optical fiber on the device may be used as a second instrument, to hold or push tissue in the eye such as during the repair of a retinal detachment.

Conventional wide-field or chandelier systems provide another illumination option for vitreo-retinal surgeons. Rather than used as an active tool, they are typically placed through the sclera so that the tip penetrates the vitreous cavity. The light delivered by these devices tends to be more diffuse and allows the surgeon to use both hands for holding other instruments. These systems often have a 100 degree field of illumination and are placed at a fixed distance from the retina but cannot provide side illumination to highlight surface texture. Further, chandeliers cast shadows when working instruments are placed in front of them and are also prone to creating glare during air-fluid exchanges such as those required during vitrectomy. Further, chandeliers are often incapable of homogenously illuminating the entire eye, and often need to be repositioned during surgery. Further, the tips of these lights are prone to melting if they come into contact with blood. In addition, the tip of these lights is in a fixed configuration and cannot be adjusted.

In contrast, devices consistent with the present disclosure may have an embodiment whereby it is placed through a fixed point in the sclera similar to a chandelier system. However, the tip of the device which is comprised of a loop of optical fiber connected to an appropriate light source, can be adjusted in size, making the loop larger or smaller to provide more or less light as needed. In one embodiment, the loop could be enlarged to encircle the entire pars plana, providing a diffuse illumination of the surgical field. In another embodiment, trocars could be placed through the pars plana at opposite poles of the eye, and the loop of the optical fiber could be held by these trocars or similar devices, thus allowing a diffuse illumination of the eye's interior. This would eliminate the problems with conventional chandelier systems such as casting shadows or failing to homogenously light the surgical field.

The present device allows surgeons to better visualize tissue, while using lower direct light levels, thereby decreasing the risk of damage to sensitive retinal photoreceptors.

In another embodiment, the device may be used as a stationary, fixed lighting system which is placed through the sclera similar to conventional chandelier lighting systems. For this, the stem is shortened to approximately 2 to 4 mm and connected to a flange which rests outside the eye. The flange prevents the light from migrating during surgery. This can be placed directly through the sclera by the surgeon, or by using conventional trocar placement systems.

During vitrectomy surgery (e.g., to peel membranes from the surface of the retina) the device could be employed to provide a diffuse, oblique illumination of the surface of the tissue. In this way, the presently disclosed device increases the contrast and visibility of the surface compared to conventional direction illumination system, even when directional light sources are used in conjunction with vital dyes. Further, the diffuse nature of the light delivered by the devices of the present disclosure enables the surgeon to place the light closer to the retina for dynamic visualization without increasing a risk of retinal photoreceptor phototoxicity. In addition, the size of the optical fiber loop can easily be adjusted directly by the surgeon intraoperatively. In addition, the loop at the tip of the device could be used as a second instrument to help stabilize tissue, such as often needed during repair of complex retinal detachments.

Similarly, an alternative embodiment of the current invention in which the device is placed through the sclera at a fixed point in a chandelier-style system can be used during surgery. This allows the surgeon to use both hand for other tools during surgery. The size of the loop at the tip of the chandelier system can similarly be adjusted to allow more or less light as needed. By enlarging the loop so that it circumnavigates the internal diameter of the pars plana, the surgeon can diffusely illuminate the vitreous cavity, thereby avoiding the shadows that typically occur with conventional systems.

Accordingly, in one embodiment the present disclosure provides a method of illuminating ocular tissue, the method comprising providing a device as disclosed herein; optionally increasing the loop length such that the loop portion has a diameter larger than an eye or a portion thereof; placing the loop portion in proximity to the eye; and reducing the loop length such that the loop portion is stationary with respect to the eye. In some embodiments, the loop is placed around at least a portion of the eye, for example the pars plana. Thus, in some embodiments, the loop portion has a diameter larger than a pars plana before placement, and is adjusted (e.g., by movement of an adjuster) to reduce the diameter of the loop portion until it is slightly larger than, about the same size as, or slightly smaller than the pars plana. In some embodiments, the loop portion is placed in proximity to retinal tissue. In some embodiments, the stem comprises a flange portion, and the method further comprising anchoring the device to the eye using the flange. In some embodiments, the method does not include administering a vital dye to the eye.

Figure 5:
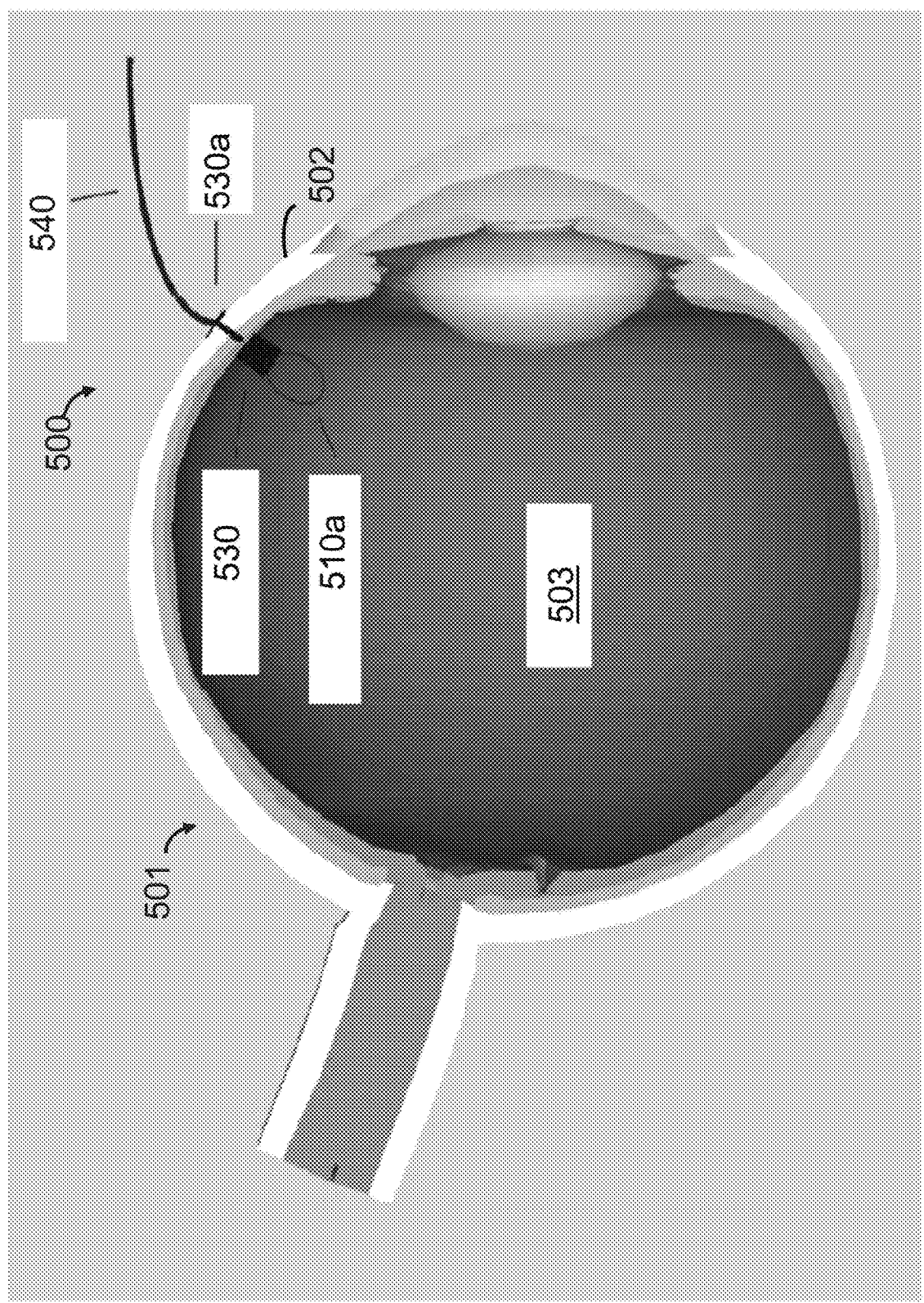
FIG. 5 is a cross sectional view of a device according to the present disclosure during a surgical procedure.

As shown in FIG. 5, a device 500 consistent with the present disclosure includes a stem 530 having a flange 530a. The stem 530 is operably connected to a fiber optic cable 540 housing an optical fiber (not labeled). The optical fiber includes a fiber optic loop portion 510a extending from a proximal end of the stem 530. In the embodiment shown in this figure, device 500 has been placed in an eye 501 such that flange 530a is adjacent to the external surface 502 of the eye 501 (e.g., the sclera), enabling the stem 530 and the fiber optic loop portion 510a to extend through the sclera, choroid and retina and into the vitreous 503.

The invention claimed is:
1. A device, comprising:
a tube having a proximal end, a distal end, and a lumen extending from the distal end to the proximal end, wherein the tube is four to six inches in length; and
an optical fiber (a) that extends through the lumen from the distal end to the proximal end of the tube and (b) that has a proximal tip portion positioned in the tube such that the optical fiber forms a loop at the proximal end of the tube.
2. The device of claim 1, further comprising an adjuster operably connected to the proximal tip portion of the optical fiber.

3. The device of claim 2, wherein the adjuster and the proximal tip portion of the optical fiber are arranged such that movement of the adjuster changes a size of the loop.
4. The device of claim 2, wherein the adjuster is positioned at least in part in the tube.
5. The device of claim 2, wherein the adjuster includes a button, a lever, or a sliding shaft.
6. The device of claim 2, wherein the adjuster includes a sliding cover positioned over the tube and configured to be advanced or retracted relative to the tube.
7. The device of claim 1, wherein:
the optical fiber has a distal tip portion opposite the proximal tip portion; and
the distal tip portion is configured to be coupled to a light source.
8. The device of claim 7, wherein the light source is an endoscope.
9. The device of claim 1, wherein the optical fiber is configured to emit light from a wall or a side of the optical fiber at least along a portion of the optical fiber corresponding to the loop.
10. The device of claim 1, wherein:
the optical fiber is a first optical fiber, the proximal tip portion is a first proximal tip portion, and the loop is a first loop;
the device further comprises a second optical fiber different from the first optical fiber; and
the second optical fiber (a) extends through the lumen from the distal end to the proximal end of the tube and (b) has a second proximal tip portion positioned in the tube such that the second optical fiber forms a second loop at the proximal end of the tube.
11. The device of claim 1, wherein the tube has a circular, oval, ellipse, square, or rounded square cross-section.
12. The device of claim 1, wherein a gauge of the tube falls within a range including 18 gauge to 30 gauge.
13. A system, comprising:
a device having a stem and an optical fiber,
wherein the stem includes a distal end, a proximal end, and a lumen extending from the distal end to the proximal end, wherein the stem is four to six inches in length, and
wherein the optical fiber (a) extends through the lumen from the distal end to the proximal end of the stem and (b) has a proximal end portion housed within the stem such that the optical fiber forms a loop at the proximal end of the stem; and
a light source operably coupled to a distal end portion of the optical fiber.
14. The system of claim 13, wherein the device further comprises an adjuster (a) operably connected to the proximal end portion of the optical fiber and (b) configured to adjust a size of the loop via movement of the adjuster.
15. The system of claim 13, wherein the optical fiber is configured to emit light from a wall or a side of the optical fiber at least along a portion of the optical fiber corresponding to the loop.
16. The system of claim 13, further comprising:
an adapter; and
a cable (a) operably connecting the distal end of the stem to the light source via the adapter and (b) housing at least the distal end portion of the optical fiber.
17. The system of claim 13, further comprising a flange configured to anchor the device in or through tissue.
18. The system of claim 13, further comprising one or more trocars, wherein:

the device is configured to pass through at least one trocar of the one or more trocars; or a trocar of the one or more trocars is configured to hold the loop of the optical fiber.

\* \* \* \* \*